United States Patent [19]

Meindersma et al.

[11] Patent Number: 5,501,797
[45] Date of Patent: Mar. 26, 1996

[54] PROCESS FOR RECOVERY OF RAW MATERIALS IN THE ASPARTAME PREPARATION PROCESS

[75] Inventors: Geert W. Meindersma, Stein; Franciscus H. P. Vergossen, Echt, both of Netherlands

[73] Assignee: Holland Sweetener Company V.o.F., Netherlands

[21] Appl. No.: 298,708

[22] Filed: Aug. 30, 1994

[51] Int. Cl.⁶ .................................................. B01D 61/00
[52] U.S. Cl. .................... 210/651; 210/652; 210/653; 210/636; 210/639; 127/34; 127/42
[58] Field of Search .................... 210/651, 652, 210/653, 654, 321.72, 636, 490, 639, 500.27; 127/34, 42, 55; 426/330; 435/68.1

[56] References Cited

U.S. PATENT DOCUMENTS

| | | | |
|---|---|---|---|
| 3,786,039 | 1/1974 | Ariyoshi. | |
| 4,116,768 | 9/1978 | Isowa et al.. | |
| 4,259,183 | 3/1981 | Cadotte | 210/654 |
| 4,806,244 | 7/1987 | Guilheim | 210/638 |
| 5,147,533 | 9/1992 | Waite | 210/490 |
| 5,277,819 | 1/1994 | Abrams | 210/636 |
| 5,304,307 | 4/1994 | Linder et al. | 210/500.38 |
| 5,350,681 | 9/1994 | Iacobucci et al. | 435/68.1 |

FOREIGN PATENT DOCUMENTS

| | | |
|---|---|---|
| 0137877 | 7/1985 | European Pat. Off.. |
| 248416 | 12/1987 | European Pat. Off.. |
| 313100 | 4/1989 | European Pat. Off.. |
| 0476875 | 9/1992 | European Pat. Off.. |
| 63375 | 11/1974 | Japan ........ 210/636 |
| 106387 | 9/1978 | Japan ........ 210/636 |
| 022905 | 2/1985 | Japan ........ 210/636 |
| 78403 | 4/1986 | Japan ........ 210/636 |
| 62-153298 | 7/1987 | Japan. |
| 9214539 | 9/1992 | WIPO. |

OTHER PUBLICATIONS

Chemical Abstracts, vol. 108, No. 7, Feb. 15, 1988, p. 780, 108:56620t.

Primary Examiner—Ana M. Fortuna
Attorney, Agent, or Firm—Cushman Darby & Cushman

[57] ABSTRACT

A process is described for the recovery of raw materials in the aspartame preparation process from aqueous process streams which also contain dissolved salt. The process comprises subjecting the streams to nanofiltration with the aid of a composite membrane having specified retention values to obtain a retentate. The raw materials present in the retentate are recovered or the retentate is returned to the aspartame preparation process without any further processing. An apparatus for carrying out the process is also described.

13 Claims, 1 Drawing Sheet

PROCESS FOR RECOVERY OF RAW MATERIALS IN THE ASPARTAME PREPARATION PROCESS

BACKGROUND OF THE INVENTION

1. Field of the Invention

The invention relates to an aspartame preparation process. More particularly, the invention relates to a process and an apparatus for the recovery of raw materials from aqueous process streams that contain dissolved salt with use of a nanofiltration membrane.

2. Description of Related Art

Aspartame is an α-dipeptide ester, L-aspartyl-L-phenylalanine methyl ester ("APM"). APM is an important synthetic low-calorie sweetening agent that is about 200 times as sweet as sugar and has an exceptionally good taste pattern without, for instance, a bitter aftertaste. The sweetener is used in a wide range of products such as soft drinks, sweets, table-top sweeteners, pharmaceutical products and the like.

Aspartame can be prepared by various routes. There exist, for instance, routes whereby (N-protected) L-aspartic acid or the anhydride thereof and (L-)phenylalanine or the methyl ester thereof are chemically coupled. Optionally, the protecting group is removed later, and APM is obtained by esterification. An example of such a process is described in, for instance, U.S. Pat. No. 3,786,039.

Enzymatic processes exist whereby, for instance, N-protected L-aspartic acid and (DL-)phenylalanine methyl ester are selectively coupled to form the LL-dipeptide derivative and subsequently converted to APM. Such a process is described in, for instance, U.S. Pat. No. 4,116,768.

Raw materials often used in the manufacture of APM include: (1) L-aspartic acid ("Asp"), (2) L-aspartic anhydride ("AspAnh"), (3) N-protected derivatives thereof with protecting groups such as formyl ("F") and benzyloxycarbonyl ("Z"), for instance F-AspAnh and Z-Asp, and (4) L- or DL-phenylalanine ("Phe") and the methyl ester thereof ("PM"). These raw materials are not fully converted in the aspartame preparation processes. In addition, these might be reformed from decomposition during downstream steps of the preparation process.

In addition, other decomposition products such as, for example, 3-benzyl-6-carboxymethyl-2,5-diketopiperazine ("DKP") or L-aspartyl-L-phenylalanine ("AP") can be formed in downstream steps in the preparation process for APM. Still other undesired by-products can be formed, including the β-form of APM (β-APM) and products in which the free aspartyl carboxyl group of the dipeptide or dipeptide ester has been esterified. The latter dipeptide esters are also referred to as AP(M) and $APM_2$.

For reasons of process economy, aspartame processes generally involve a large number of recirculation streams. During the preparation and work-up of aspartame, the various process streams undergo pH changes resulting from the addition of acids and bases. These changes result from, among other things, the addition of acids and bases for the removal of protecting groups. Also, pH changes can result from addition of acids and bases for purification, or for precipitation of, for instance, the Z-APM.PM addition product or the APM.HCl salt or any other addition product or crystallizing salt, or for recovery of APM by crystallization at a pH of 4.0 to 5.5.

The result is that various process streams contain inorganic salt or salts in addition to the starting materials and/or decomposition products already mentioned. In general, the process streams are aqueous, although the process streams may also contain organic solvents. Sodium chloride, for instance, is often present in amounts greater than about 1 wt. %, and very often in amounts as large as 10 or 25 wt. %. Streams of enzymatic processes may in addition contain small amounts of enzyme.

Various methods of recovering raw materials and/or removing decomposition products from process streams of aspartame preparation have been suggested or described. For instance, EP-A-0,476,875 describes methods for purification and concentration of biologically active materials from mixtures that contain organic solvents using solvent-stable membranes. Membrane processes are described in EP-A-0,476,875 which may be considered as "nanofiltration" membrane processes, using recent terminology. However, the term "nanofiltration" is not used in the specification, and the specification is not focused on the separation of low molecular weight organic compounds from salts.

EP-A-0,476,875 describes examples of concentrating very dilute (only 500 ppm) aqueous solutions of APM with use of membranes. However, there is no teaching or suggestion that such concentrating steps with use of membranes could be used favorably for treating dilute or concentrated APM solutions that contain amounts of salt higher than 2,000 ppm. In other words, EP-A-0,476,875 does not describe an effective method for treatment of aspartame solutions in the presence of high amounts of salt. The membranes of this reference appear to have high retention for salts; retention of salt is about 80% as calculated from the Examples. Accordingly, the membranes appear ill-suited for lowering the amount of salt in the retentate.

Other serious limitations for the process described in EP-0-476,875 exist. For example, it is evident from the examples on purification of penicillin G that the performance of the solvent-stable membranes does not vary over a broad range of pH values (from 0.5 to 12). However, performance sharply deteriorates at higher pH.

Other membrane processes related to the aspartame preparation process are known. For instance, EP-A-0,313,100 describes an electrodialysis process in which organic acids such as DKP and AP are removed.

According to JP-A-62-153,298, APM can be purified from low-molecular weight electrolytes by a dialysis process. A solution of APM in water at a pH of 3–7 and a temperature of 0°–80° C. was contacted with an amphoteric ion exchange membrane that allowed the low-molecular weight electrolytes to pass. The volume of the original solution was retained. In this type of process, an increase in pressure does lead to a desired increase in concentration. However, it also leads to unwanted permeation losses of organic products. Moreover, in a dialysis process, the dialyzate always needs to be replaced, which is quite cumbersome.

Also, EP-B-0,248,416 describes a salt removal process which—at elevated pressure—operates on the principle of reverse osmosis. That process utilizes neutral membranes such as polyamide acetate, polysulfone acetate and cellulose acetate membranes with 30–80% salt retention. At a lower salt retention, such membranes are not suitable because too much organic material will be transported. Hence, there will be no fractionating effect with respect to molecules larger than 100 D, wherein D is Dalton, or ¹⁄₁₆th the mass of the oxygen-16 isotope. Moreover, in such a reverse osmosis process, the extent to which the starting solution can be concentrated is limited inasmuch as the osmotic pressure strongly increases during the process.

The raw materials and other products still to be recovered often are present in relatively dilute streams. The presence of salt in the streams, however, makes it difficult to concentrate the streams by evaporation. Given the unfavorable weight ratio of organic components and salt, evaporation is expected to result in salt crystallization or cocrystallization with organic components. Moreover, undesired side-reactions may take place, which can result in strong discoloration.

None of these work-up processes has been found to be generally suitable for recovering raw materials from those aqueous process streams in the aspartame preparation processes which contain relatively high amounts—at least 1 wt. %—of salt. Moreover, processes such as dialysis or electrodialysis, reverse osmosis and treatment with an ion exchanger are relatively cumbersome and undesirable on an industrial scale. Furthermore, in many of the prior art methods, the solution started from can be concentrated only to a limited extent.

As a consequence, those skilled in the art have had a need for a process that does not suffer these drawbacks and enables the raw materials under consideration to be recovered easily and efficiently in a process involving simultaneous salt removal from the process streams and concentration of the organic components in them.

A general review of membrane technology can be found in the article entitled "Membranes and Membrane Separation Processes" found in Ullmann's *Encyclopedia of Industrial Chemistry* (VCH, 1990). Also, nanofiltration membrane technology is described in Chemical Engineering Progress, pgs. 68–74 (March, 1994).

SUMMARY AND OBJECTS OF THE PRESENT INVENTION

Objects for the present invention include a process in which materials should be facilely and efficiently recovered, while simultaneously removing salt from the process streams in APM preparation processes and concentrating the organic components in the de-salted residual process streams. These and other objects are satisfied by the present process for treatment of various process streams in the aspartame preparation processes.

In the present invention, at least one of the aqueous process streams in aspartame production having a salt content of at least 1 wt. % is subjected to nanofiltration with the aid of a composite membrane having a retention between about 50 and about 100% for components having a molecular weight greater than about 100 Daltons and showing a retention between about +20 and about −40% for monovalent salts to obtain a retentate. The raw materials present in the retentate so obtained are recovered by a manner known in the art or the retentate is returned to the aspartame preparation process without any further processing.

The present invention also provides for an apparatus for recovering raw materials from aqueous process streams in an aspartame preparation process which are obtained after separation of aspartame and which contain dissolved salt. The apparatus comprises at least one module having at least one composite membrane with a retention between about 50 and about 100% for components having a molecular weight higher than about 100 Daltons and a retention between about +20 and about −40% for monovalent salts, and which forms a partially permeable separation between a feed side, to which the process streams to be treated are fed under superatmospheric pressure and the retentate results, and a discharge side, where the permeate obtained is either collected or discharged or optionally externally recirculated to the feed side.

Advantages of the present invention are found in that salt is easily and efficiently removed, and raw materials are easily and efficiently recovered. Organic components in the process stream or streams are concurrently concentrated. High flux is achieved at high pH. Excellent results are found over a broad range of pH values. High retention values for organic compounds are obtained in the presence of salts.

DETAILED DESCRIPTION OF THE PRESENT INVENTION

Figure 1:
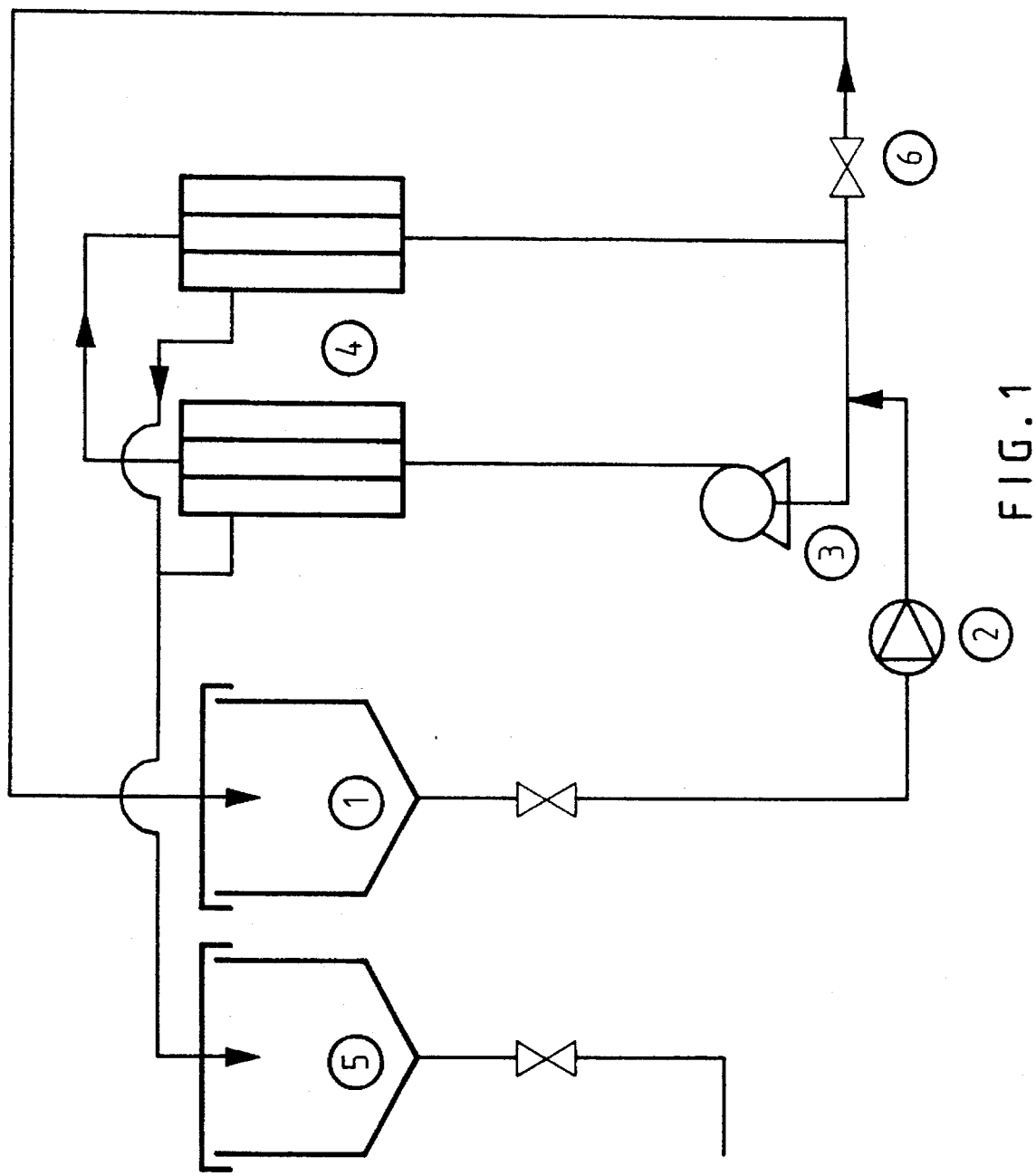
FIG. 1 illustrates schematically the claimed process and will be described in full detail hereinafter.

For the purposes of the present invention, nanofiltration is sometimes referred to as loose reverse osmosis, and means the application of membranes possessing both reverse osmosis and fractionating properties with respect to molecules larger than about 100 Daltons. Membranes used in the context of the invention should therefore possess properties which render them suitable for application in reverse osmosis and for application in fractionating molecules larger than about 100 Daltons. These requisites are satisfied by composite membranes having a retention between about 50 and about 100% for components having a molecular weight of about 100 Daltons or more and showing a low retention between about +20 and about −40% for monovalent salts.

The per cent retention of a component i ($R_i$) is given by the formula $R_i=(1-C_{ip}/C_{ir})\times100\%$, wherein $C_{ip}$ is the concentration of component i in the permeate and $C_{ir}$ is the concentration of component i in the retentate, both expressed in wt. %. The percent retention of a component can also be called the membrane rejection coefficient.

By present preference, the composite membranes have a substantially negatively charged selective top layer which has been applied to an ultrafiltration membrane as supporting layer. Such membranes are commercially available, and can be referred to as thin film composites ("TFC"). Membranes suitable for the purpose of the invention include for instance the SelRo®-type (Kiryat Weizmann Ltd.), DRC-1000® (Celfa), NF-PES-10/PP60® (Kalle), NTR 7410® (Nitto) and WFN 0505® (Stork Friesland—now under development).

Nanofiltration is described in *Nederlandse Membraangide* (Dutch Membrane Guide) (February 1993) and in Rautenbach et al., Separation Potential of Nanofiltration Membranes, *Desalination*, 77:73 (1990). Nanofiltration is also described in U.S. Pat. No. 4,806,244, the complete disclosure of which is incorporated herein by reference. Properties and performance characteristics of nanofiltration membranes are described in *Chemical Engineering Progress*, pgs. 68–74 (March, 1994), the complete disclosure of which is incorporated herein by reference. References cited in this *Chemical Engineering Progress* article are also of interest for describing nanofiltration membranes.

The nanofiltration technique is applicable to retention of organic compounds having a molecular weight in the range of about 200 to 1,000 Daltons, and also to ions having a valency greater than 1. This technique is conducted at pressures which are relatively low, such as 3 to 20 bar, in comparison to reverse osmosis, while the flux is high.

In the composite membranes contemplated herein, polymers suitable for the top layer include, among others, polyamide, polyvinyl alcohol, sulfonated polysulfone, and sulfonated polyether sulfone. In principle, ultrafiltration membranes can, as described elsewhere herein, be used as the supporting layer in the composite structure For the present invention, the term "aspartame" includes other dipeptide sweeteners such as L-aspartyl-D-alaninyl-2,2,4,4-tetramethylthietanyl amide (alitame) and dipeptides in general. Likewise, as to the raw materials to be recovered, the invention is not limited to such raw materials as are used in known aspartame preparation processes, but also includes raw materials which are not used as building blocks for aspartame but which can be used for other dipeptides. The invention equally includes the recovery of raw materials for aspartame preparation such as Phe, Z-Asp, Asp, PM and the like from recirculation streams or waste streams which occur in the preparation processes for those same raw materials.

If streams contain substantial amounts of APM, it is recommended first to recover the APM. The present invention also relates to streams containing relatively small amounts of dissolved APM—before or after removing the bulk of APM—and also to streams with little or no APM. Any APM present in the process streams may be regarded as product that can be recovered, whether or not by way of conversion to the raw materials.

Process streams containing only very small amounts of raw materials can be, but need not be, subjected to this recovery process according to the invention. Nor, in general, need the permeate streams that are obtained in applying the process and that contain far lower raw materials concentrations than the treated process streams be subjected to a second treatment according to the invention. If they are of acceptable quality, the retentate streams obtained may be: 1) returned to the preparation process, whether or not after adjusting of, for instance, the pH and/or temperature, but usually without any further processing, or 2) utilized to recover the desired components by commonly known methods. Those skilled in the art will be able to establish which process streams are, and which process streams are not, suitable for such a nanofiltration treatment, depending on the desired economy of the overall process.

The process according to the invention is particularly suitable for recovering Z-Asp, F-Asp, Asp, AspAnh, Phe and PM from aqueous streams of the aspartame process. The choice of the pH at which nanofiltration is effected may affect the composition of the streams. At a pH>7, for instance, PM will hydrolyse and Phe can be recovered.

The process can be operated batch-wise or continuously. This can be effected in apparatus similar to that employed for reverse osmosis and ultrafiltration. Such apparatus generally comprise one or more membrane modules through which the liquid is pumped under pressure by one or more pumps. The membranes contemplated herein have a retention between 50 and about 100% in components having a molecular weight of about 100 Daltons or more and showing a low retention between about +20 and about −40% for monovalent salts.

Processes for the preparation of aspartame include many streams that may be treated according to the present invention. Examples of components that may occur in such streams include, but are not limited to, PM, AP, DKP, Z-Asp, Asp, AP(M), $APM_2$, APM, F-Asp, Phe, etc. The concentrations in which these substances occur vary depending on the process or the process section in which the stream is present and may vary widely depending on the solubility, temperature, pH and so forth.

Concentrations of these components commonly are in the range of 0.1–5 wt. %. Some streams, particularly in enzymatic processes, may also contain some enzyme. An enzyme process is described in U.S. Pat. No. 4,116,768, the complete disclosure patent is incorporated herein by reference.

In the process according to the present invention, the process stream/streams to be treated is/are supplied individually or collectively to one side of a membrane module. The nanofiltration membrane effects the separation between this side of the module and the other side. At the other side, or discharge side, the permeate, which has passed through the membrane and has largely been cleared of organic compounds of about $Mw \geq 100$ D, can be discharged. If tubular membranes are employed, the process stream/streams to be treated is/are supplied on the inside of the tube and discharged on the outside, or the other way round. Spiral-wound, hollow-fiber, plated cartridge filter modules, capillary or flat membranes may also be used. Practical considerations will dictate the dimensions and type of module used.

Thus, on the inlet side a retentate solution is obtained in which the organic components are more concentrated and in which the ratio of the organic components and salt is much improved. The raw materials can be recovered from this retentate by simple, commonly known methods such as evaporative recrystallization, extraction optionally followed by crystallization, ion exchange methods and pH-shift techniques. It is also possible to return the retentate solution to the process.

If the organic components are present in relatively high concentrations, one or more of such components may crystallize to some degree as the retentate solution is being concentrated. This has not been found to be unfavorable for the process of the invention, as will also be evident from the examples described hereinafter.

The permeate flux and/or the separation efficiency may be improved still further by proper adjustment of the pH and pressure on the inlet side of the nanofiltration membrane. Flux (Fp) in kg/m².h is the amount of permeate passing through a unit area of the membrane unit per unit time. Separation efficiency (selectivity) is the ratio of the mixture composition in the permeate $(C_{salt}/C_{organic})_P$ versus the mixture composition in the feed $(C_{salt}/C_{organic})_F$. Preferably, a pH≥4 is chosen and the system is operated at a pressure on the inlet side which is higher than atmospheric, and preferably higher than 1 MPa (1 MPa=10 bar=10 bar abs.). The upper limits of pH, temperature and pressure depend in part on the properties of the membrane. As far as the pH is concerned, the invention yields excellent results, particularly at pH 8–11.

The temperature at which nanofiltration is effected is generally not believed to be critical and is often between 0° and 80° C., depending on the membrane. Ambient temperature is particularly suitable. However, at higher temperatures, a higher flux is attained because of the favorable viscosity of the streams. Higher temperatures may be advantageous.

The performance of the nanofiltration process according to the invention can be established by determining: (1) the concentration factor (Cf), which is the quotient (ratio) of the original amount (feed) and the remaining amount (retentate), and (2) the retention for each of the desired components ($R_i$), and (3) the permeate flux (Fp) in kg/m².h, which is the amount of permeate passing through a unit area of the membrane per unit time.

The concentration factor Cf is related to the term "recovery rate" (defined as the ratio between filtrate volume and volume of the initial feed solution). The recovery rate is the ratio between permeate volume and initial volume. The retentate volume plus the permeate volume equals the initial volume. The recovery rate is also related to operational factors such as pH, pressure, temperature and salt concentration.

Fp is measured by determining the amount of stream passing through the membrane in a certain time and dividing this amount by the actual surface area of the membrane and the time. Flux also may be expressed in liter/$m^2$.h instead of kg/$m^2$.h.

The membranes may be readily cleaned either after use or after the permeability of the membrane diminishes. Cleaning can be effected at a slightly elevated temperature if so desired, by rinsing with water or a caustic solution. If the streams contain small amounts of enzyme, rinsing in the presence of small amounts of surfactant, for instance Ultrasil®, might be useful.

In addition, less expensive prefilters (100–200 μm) can be used to protect the more expensive nanofiltration membranes. Other cleaning agents can, if desired, be used. The choice of cleaning method will depend on the membrane being cleaned, and the membrane manufacturer's instructions should be consulted.

The cleaning can be accomplished with a forward flushing or a backward flushing.

The higher the pressure, the higher the permeate flux will be. An increase in pH will also result in higher flux. Increasing pH from about 4–6 to about 8–9 leads to an increase in values found for the retention ($R_j$) of the organic components and a decrease in the retention for salts. At pH>9.9, hardly any effect on the retention ($R_j$) is observed. Increasing the pressure also leads to an increase in the retention figure for the raw materials, e.g., organic components.

The higher the value of Cf, which is chosen by adjusting the process conditions, the greater in absolute terms is the portion of raw materials that will be discharged via the permeate, so that the amount of raw materials to be reclaimed from the retentate will decrease. Therefore, if more raw material is to be recovered via the retentate, a lower concentration factor should be chosen. In that case, the membrane area may be smaller than would be necessary for attaining a higher Cf.

It is possible for those skilled in the art to determine favorable settings enabling the desired results and economy of the process to be achieved.

The nature of any salt or salts present in the streams also affects the retention thereof. In general, the retention is lower for monovalent salts. Since the nature of the salt in the process streams is dependent on the acids and bases used in the various process steps of the aspartame preparation process, it is preferred to use monovalent acid radical ions and metal ions so that sodium chloride, for instance, is formed as salt.

It is also possible to recirculate the permeate obtained and to add it to the stream to be subjected to nanofiltration or to subject it again to a separate nanofiltration treatment. In that way, the amount of the raw materials to be recovered can be increased further.

It has been found that, even if the concentration of the raw materials in the streams to be subjected to nanofiltration according to the invention becomes so high during nanofiltration that one or more of such raw materials crystallizes, the performance of the nanofiltration in terms of the retention effect is not affected. However, the permeate flux will diminish as a result of crystals precipitating on the membrane surface.

Additional amounts of salt can be removed while continuing the nanofiltration and without any decrease in permeate flux by adding water or a buffer solution on the inlet side just before crystallization can take place. In that case, a combination of nanofiltration and diafiltration is applied. Even when there is no question of crystallization, this method may be applied for further removal of salt from the retentate. Aqueous buffer solutions can be used.

In this application the term bar abs. means absolute pressure in bar (1 bar equals 0.01 Mpa).

A purification process used in aspartame preparation has been described in Belium Application 093 00889 filed Aug. 30, 1993 in Belgium, the complete disclosure of which is incorporated herein by reference.

The invention will be further clarified by a consideration of the following examples, which are intended to be purely exemplary of the use of the invention. All of the experiments described hereinbelow were carried out in a rig as depicted in FIG. 1.

In FIG. 1, a 20-liter storage tank 1 contains the solution to be treated and is equipped with a stirrer. The contents of this tank are kept at a temperature of about 40° C. The retentate formed in the experiments was always returned to this tank and mixed with the tank's contents. A glass tank was used in the Examples.

A feed pump 2 has a maximum throughput of 100 l/h which pressurizes the liquid and keeps it under pressure in combination with valve 6. A three piston type pump, among others, can be used as feed pump 2. A circulation pump 3 has a throughput which is adjustable to a maximum of 1800 l/h and supplies the feed to the inside of the tubular membranes in membrane module system 4. A centrifugal pump, among others, can be used as the circulation pump 3. A membrane module system 4 has two series-arranged tubular composite membranes and separate discharge streams for permeate and retentate.

A collecting vessel 5 is provided for the permeate formed in the experiments.

A pressure control valve 6 is provided to control the pressure.

In FIG. 1, there are two valves (shown below 5 and 1) which are present to allow the practitioner to close the vessels during operations.

The lines used in the apparatus are formed stainless steel (316SS) and the storage vessel is a glass vessel.

Prior to each of the following experiments 10–20 liters of an aqueous, salt-containing, representative process stream was prepared by adding one or more organic components, NaCl and 22% NaOH solution until the concentrations listed in Tables 1 and 3 were obtained. The concentrations of the organic components were determined with the aid of HPLC (high pressure liquid chromatography) and the chloride concentration was determined with the aid of ion chromatography. The pH was measured at the temperature of the solution. Monitoring of pH occurred in the storage vessel, No. 1.

The measurement of concentrations is done at the start of the experiments, and also during the course thereof, in order to determine retention values.

In all nanofiltration experiments, the starting solution was charged to the storage tank at 40° C., whereupon the feed pump and the circulation pump were started. During most experiments a pressure of 30 bar was maintained. However, in some cases a different pressure setting was applied, as indicated.

Example I. Use of SelRo MPT 10® Membrane

A set of experiments were carried out with the aid of a PCI Microlab 80 membrane module (FIG. 1, No. 4) in which two tubular SelRo MPT 10® membranes with a diameter of 12.5 mm and a length of 1.2 m were arranged in series.

The starting solutions used in experiments 1–6 are listed in Table 1. All experiments were carried out at a pressure of 30 bar, 40° C. and a maximum throughput of the pumps. Table 1 also gives the composition for comparative experiment A, which is described hereinafter.

TABLE 1

| | composition in wt. % | | | | |
|---|---|---|---|---|---|
| | Phe | PM | Z—Asp | Cl⁻ | pH |
| 1 | 1.18 | 0.64 | 0.64 | 7.18 | 4.6 |
| 2 | 1.2 | — | 0.65 | 6.5 | 8.4 |
| 3 | 1.8 | — | 0.63 | 6.3 | 9.9 |
| 4 | 1.44 | — | — | 10.10 | 6.1 |
| 5 | 1.35 | — | — | 9.84 | 8.1 |
| 6 | 1.02 | — | 1.02 | 11.89 | 9.8 |
| A | 1.06 | 0.52 | 0.50 | 7.86 | 4.6 |

During the experiments no change in pH was observed. The results of the experiments in terms of permeate and retentate composition after the point where the targeted, or achieved, concentration factor Cf (also indicated) was reached (when the experiment was stopped) are summarized in Table 2. Table 2 also includes the values of $R_i$, Cf and Fp for the end situation. The pH was monitored in the storage vessel. The results of Comparative Example A (see below) are also included.

Example II. Use of WFN 0505® Membrane

In the same way as described above for SelRo MPT10® membrane, experiments were performed in a membrane module which had been slightly modified because of the different diameter and length of the membranes (FIG. 1, No. 4).

Each of the WFN tubular membranes was 14.4 mm in diameter and 1.8 m long.

The starting solutions in these experiments are listed in Table 3. The results of the experiments are given in Table 4. These experiments were also carried out at 30 bar and 40° C.

In experiments I and II, no difference in $R_i$ was observed before and after crystallization.

TABLE 3

| | Composition in wt. % | | | | |
|---|---|---|---|---|---|
| | Phe | PM | Z—Asp | Cl⁻ | pH |
| 7 | 1.00 | 0.51 | 0.91 | 7.21 | 4.6 |
| 8*) | 1.59 | — | 0.98 | 6.40 | 9.9 |
| 9*) | 1.59 | — | 0.98 | 6.40 | 10.6 |

*) During these nanofiltration experiments, the pH was kept constant by adding small amounts of 22% NaOH solution in order to avoid changes in pH.

TABLE 2

| | Cf | Fp kg/m². | permeate (wt. %) | | | | retentate (wt. %) | | | | $R_i$ (%) | | | |
|---|---|---|---|---|---|---|---|---|---|---|---|---|---|---|
| | [–] | hr | Phe | PM | Z—Asp | Cl⁻ | Phe | PM | Z—Asp | Cl⁻ | Phe | PM | Z—Asp | Cl⁻ |
| 1 | 4.0 | 21 | 0.73 | 0.59 | 0.36 | 7.70 | 2.80 | 1.28 | 1.94 | 7.50 | 74 | 54 | 81 | –3 |
| 2 | 5.8 | 27 | 1.2 | — | 0.24 | 6.80 | 4.40 | — | 3.01 | 5.78 | 73 | — | 92 | –18 |
| 3 | 5.1 | 49 | 1.6 | — | 0.25 | 6.60 | 4.40 | — | 2.42 | 5.50 | 64 | — | 90 | –20 |
| 4 | 3.7 | 58 | 0.9 | — | — | 10.50 | 2.63 | — | — | 9.28 | 66 | — | — | –13 |
| 5 | 4.3 | 70 | 0.89 | — | — | 10.3 | 2.14 | — | — | 9.18 | 58 | — | — | –12 |
| 6 | 3.9 | 55 | 0.8 | — | 0.8 | 12.38 | 2.50 | — | 2.70 | 10.23 | 68 | — | 70 | –21 |
| A | 1.3 | 25 | 0.31 | 0.29 | 0.06 | 5.42 | 1.29 | 0.59 | 0.64 | 8.61 | 76 | 51 | 91 | +37 |

In some of these examples (Nos. 1 and 2), Phe had crystallized in the retentate during the experiment. This did not affect the $R_i$ values.

TABLE 4

| | Cf | Fp kg/m². | permeate (wt. %) | | | | retentate (wt. %) | | | | $R_i$ (%) | | | |
|---|---|---|---|---|---|---|---|---|---|---|---|---|---|---|
| | [–] | hr | Phe | PM | Z—Asp | Cl⁻ | Phe | PM | Z—Asp | Cl⁻ | Phe | PM | Z—Asp | Cl⁻ |
| 7 | 2.1 | 68 | 0.31 | 0.30 | 0.17 | 6.90 | 1.73 | 0.72 | 1.69 | 7.31 | 82 | 58 | 90 | –6 |
| 8 | 2.0 | 141 | 0.54 | — | 0.04 | 6.50 | 2.45 | — | 1.80 | 6.10 | 78 | — | 98 | –7 |
| 9 | 4.5 | 50 | 0.74 | — | 0.08 | 4.40 | 4.31 | — | 4.70 | 3.16 | 83 | — | 98 | –39 |

Sodium hydroxide was used merely in order to exclude any effects in experimental results due to fluctuation in pH. However, constant pH is not a required, critical, or preferred parameter for this invention.

Example III. Use of Diafiltration with Nanofiltration

Experiments analogous to examples 1 and 2 were carried out. However, the compositions were slightly different, and the experiments were in part carried out under different pressures. The Phe concentration was kept relatively low by additions of water at 40° C. Phe can crystallize at a concentration of around 2 wt. %, although the wt. % for crystallization depends on the composition of the solution. The amount of water added in these experiments was about 50 wt. % relative to the amount of retentate present at the time the addition was made. Crystallization can be determined visually in the glass storage vessel which receives the returning retentate.

The membranes used in Example III were SelRo MPT10 membranes.

The results of these experiments, which were started with the compositions listed in Table 5, are given in Table 6 for the situations before and after addition of water as well as for the end situation (a, b and c, respectively).

The water was added in only one shot. The water addition related to extra removal of NaCl to avoid crystallization of L-Phe at about 2% concentration. The designations a, b, and c refer, respectively to the situation before water addition, after water addition and the final situation.

Experiment 10 was carried out at 30 bar and 40° C.; experiment 11 at 20 bar and 40° C.

TABLE 5

| | Composition in wt. % | | | | |
|---|---|---|---|---|---|
| | Phe | PM | Z—Asp | Cl⁻ | pH |
| 10 | 1.16 | 0.48 | 0.47 | 5.47 | 4.6 |
| 11 | 1.86 | — | 0.52 | 6.40 | 8.4 |

In experiment 11 some crystallization of Phe occurred before water was added. Due to the dilution, the crystals could be redissolved. In the end, a Cf of 2 could still be achieved, without any crystals being present.

Comparative Example A

For comparison, a neutral AFC 30 polyamide membrane from PCI was used in a reverse-osmosis experiment in a BUF unit containing 18 of these tubular membranes with two sequences of 9 series-arranged membranes being arranged in parallel, the total length being 1.2 m and the diameter being 12.5 mm (total membrane surface area 0.9, m²).

The compositions at the start and at the end of the experiments are listed in Tables 1 and 2.

A BUF unit is an expression which refers to bench-scale ultrafiltration unit. The retentions of this membrane in this comparative example are, respectively, 98.5% for lactose (mol. wt. 341) and 35% for NaCl at 0.2% concentration.

While the invention has been described in detail and with reference to specific embodiments thereof, it will be apparent to persons having ordinary skill in the art that various changes and modifications can be made therein without departing from the spirit and scope thereof.

What is claimed is:

1. A process for recovering raw materials from an aqueous process stream from the production of aspartame, wherein said aqueous process stream contains dissolved salt and raw materials, which process comprises subjecting to nanofiltration said aqueous process stream having a salt content of at least 1% by weight, with the aid of a composite nanofiltration membrane having a retention between about 50 and about 100% for components having a molecular weight greater than about 100 Daltons and a retention between about +20 and about −40% for monovalent salts, wherein a retentate containing the raw materials is formed, and recovering the raw materials contained in the retentate or recycling the retentate.

2. A process according to claim 1, wherein the composite membrane comprises a substantially negatively charged top layer, an ultrafiltration membrane as a support layer, and the top layer is applied to the support layer.

3. A process according to claim 1, wherein the nanofiltration is effected at a pH≧about 4 and a temperature of between about 0° and about 80° C.

4. A process according to claim 3, wherein the nanofiltration is effected at a pH between about 8 and about 11.

5. A process according to claim 1, wherein the membrane has a feed side, and the pressure at the feed side of the membrane is superatmospheric.

TABLE 6

| | Cf | Fp kg/m². | permeate (wt. %) | | | | retentate (wt. %) | | | | $R_i$ (%) | | | |
|---|---|---|---|---|---|---|---|---|---|---|---|---|---|---|
| | [−] | hr | Phe | PM | Z—Asp | Cl⁻ | Phe | PM | Z—Asp | Cl⁻ | Phe | PM | Z—Asp | Cl⁻ |
| 10a | 1.8 | 55 | 0.32 | 0.15 | 0.19 | 4.90 | 1.77 | 0.65 | 0.75 | 5.83 | 82 | 77 | 88 | +16 |
| 10b | 1.3 | 57.5 | 0.34 | 0.15 | 0.09 | 4.40 | 1.32 | 0.48 | 0.53 | 4.14 | 74 | 69 | 83 | −6 |
| 10c | 1.8 | 53 | 0.27 | 0.12 | 0.01 | 3.80 | 1.72 | 0.61 | 0.72 | 4.44 | 84 | 80 | 99 | −14 |
| 11a | 2.75 | 6 | 1.01 | — | 0.12 | 6.40 | 2.75 | — | 1.08 | 5.96 | 63 | — | 89 | −7 |
| 11b | 1.7 | 30 | 0.98 | — | 0.10 | 4.80 | 2.00 | — | 0.81 | 4.31 | 51 | — | 88 | −11 |
| 11c | 2.0 | 34 | 1.27 | — | 0.08 | 4.70 | 2.19 | — | 0.95 | 4.19 | 42 | — | 92 | −12 |

Although the retentate may, in some instances, have a chloride concentration higher than the permeate, the actual amount of chloride is less in the retentate due to chloride removal.

6. A process according to claim 5, wherein the pressure is between about 10 and about 50 bar abs.

7. A process according to claim 1, wherein the salt is a monovalent salt.

8. A process according to claim 1, wherein the process further comprises cleaning the membrane by flushing the membrane with water or a caustic solution.

9. A process according to claim 8, wherein the cleaning is conducted in the presence of a surfactant.

10. A process according to claim 1, wherein the process further comprises adding water or a buffer solution to the retentate and continuing the nanofiltration.

11. A process according to claim 1, wherein the raw materials recovered from said aqueous process stream from the production of aspartame comprise organic molecules having molecular weights up to 1000 Daltons.

12. A process according to claim 1, wherein said aqueous process stream is obtained by combining two or more process streams in the production of aspartame.

13. A process for recovering raw materials from an aqueous process stream from the production of aspartame, wherein said aqueous process stream contains dissolved salt and raw materials, which process comprises subjecting to nanofiltration an aqueous process stream having a salt content of at least 1% by weight, with the aid of a composite nanofiltration membrane having a retention between about 50 and about 100% for components having a molecular weight greater than about 100 Daltons and a retention between about +20 and about −40% for monovalent salts, wherein said composite membrane comprises an ultrafiltration membrane as a support layer and a substantially negatively charged top layer applied to said support layer, said nanofiltration being effected at a pH greater than or equal to about 4 and at a temperature of between about 0° C. and about 80° C., wherein a retentate containing the raw materials is formed, and recovering the raw materials contained in the retentate or recycling the retentate.

* * * * *